US009982521B2

(12) United States Patent
Brodie et al.

(10) Patent No.: US 9,982,521 B2
(45) Date of Patent: May 29, 2018

(54) METHOD FOR INJECTING LOW SALINITY WATER

(71) Applicant: BP EXPLORATION OPERATING COMPANY LIMITED, Middlesex (GB)

(72) Inventors: James Andrew Brodie, Middlesex (GB); Gary Russell Jerauld, Houston, TX (US)

(73) Assignee: BP EXPLORATION OPERATING COMPANY LIMITED, Middlesex (GB)

(*) Notice: Subject to any disclaimer, the term of this patent is extended or adjusted under 35 U.S.C. 154(b) by 37 days.

(21) Appl. No.: 15/188,083

(22) Filed: Jun. 21, 2016

(65) Prior Publication Data

US 2016/0298426 A1 Oct. 13, 2016

Related U.S. Application Data

(63) Continuation-in-part of application No. 14/117,414, filed as application No. PCT/EP2012/059226 on May 17, 2012.

(Continued)

(51) Int. Cl.
| | | |
|---|---|---|
| *G01N 15/08* | (2006.01) | |
| *E21B 43/20* | (2006.01) | |
| *G01N 13/00* | (2006.01) | |

(52) U.S. Cl.
CPC ............. *E21B 43/20* (2013.01); *G01N 15/08* (2013.01); *G01N 2013/003* (2013.01)

(58) Field of Classification Search
CPC ......... E21B 43/16; E21B 43/162; E21B 43/20
See application file for complete search history.

(56) References Cited

U.S. PATENT DOCUMENTS

| 4,703,797 A | 11/1987 | Djabbarah |
| 7,006,959 B1 | 2/2006 | Huh et al. |

(Continued)

FOREIGN PATENT DOCUMENTS

| CN | 1378666 A | 11/2002 |
| CN | 1529238 A | 9/2004 |

(Continued)

OTHER PUBLICATIONS

Ayiala et al. "A Designer Water Process for Offshore Low Salinity and Polymer flooding Applications", SPE 129926, Apr. 2010.*

(Continued)

*Primary Examiner* — William D Hutton, Jr.
*Assistant Examiner* — Charles R Nold
(74) *Attorney, Agent, or Firm* — Conley Rose, P.C.

(57) ABSTRACT

A computer-implemented method for configuring operating conditions for at least one of desalination equipment and fluid injection equipment to be used in a low salinity waterflood on a hydrocarbon-bearing reservoir is provided. The reservoir is penetrable by an injection well and a production well. The method comprises deriving an ion diffusion distance value from: a diffusion coefficient indicative of a rate of diffusion of ions through relatively permeable layers of the reservoir when the low salinity water is present therein; and a residence time value indicative of the time required for the low salinity water to pass from the injection well to the production well through the reservoir; comparing the thickness of the relatively permeable layers to the derived ion diffusion distance value; generating an indication of the effectiveness of performing a low salinity waterflood; and configuring said operating conditions based on the indication of the effectiveness.

18 Claims, 5 Drawing Sheets

Related U.S. Application Data (60) Provisional application No. 61/487,357, filed on May 18, 2011.

(56) References Cited

U.S. PATENT DOCUMENTS

| | | | |
|---|---|---|---|
| 7,640,981 | B2 | 1/2010 | Collins et al. |
| 7,963,327 | B1 | 6/2011 | Saleri et al. |
| 2006/0224369 | A1 | 10/2006 | Yang et al. |
| 2010/0300682 | A1 | 12/2010 | Thakur et al. |

FOREIGN PATENT DOCUMENTS

| | | |
|---|---|---|
| CN | 101023242 A | 8/2007 |
| WO | 2007/081577 A2 | 7/2007 |
| WO | 2008/029124 A1 | 3/2008 |
| WO | 2010/138558 A2 | 12/2010 |
| WO | 2010/139932 | 12/2010 |

OTHER PUBLICATIONS

Jerauld et al. SPE 102239 "Modeling Low-Salinity Waterflooding" 2006.*
Wu et al. SPE 118830 "Efficient Simulation for Low-Salinity Waterflooding in Porous and Fractured Reservoirs", Feb. 2009.*
Chinese Office Action dated Sep. 30, 2015, for Chinese Application No. 201280035657.0 (6 p.).
English Translation of Chinese Office Action dated Sep. 30, 2015, for Chinese Application No. 201280035657.0 (8 p.).
Restriction Requirement dated Jul. 10, 2015, for U.S. Appl. No. 14/117,414 (5 p.).
Response to Restriction Requirement dated Jul. 10, 2015, for U.S. Appl. No. 14/117,414; Response filed Aug. 5, 2015 (2 p.).
Office Action dated Nov. 18, 2015, for U.S. Appl. No. 14/117,414 (23 p.).
Response to Office Action dated Nov. 18, 2015, for U.S. Appl. No. 14/117,414; Response filed Feb. 17, 2016 (23 p.).
Final Office Action dated May 27, 2016, for U.S. Appl. No. 14/117,414 (23 p.).

* cited by examiner

METHOD FOR INJECTING LOW SALINITY WATER

CROSS-REFERENCE TO RELATED APPLICATIONS

This application is a continuation-in-part of U.S. application Ser. No. 14/117,414 filed on Nov. 13, 2013, and entitled "Method for Injecting Low Salinity Water," which is the U.S. national phase of International Application No. PCT/EP2012/059226 filed May 17, 2012, which designated the U.S. and claims priority to U.S. Provisional Application No. 61/487,357 filed on May 18, 2011, the entire contents of each of which is incorporated herein by reference for all purposes.

STATEMENT REGARDING FEDERALLY SPONSORED RESEARCH OR DEVELOPMENT

Not applicable.

BACKGROUND

Field of the Invention

This invention relates to systems and methods for configuring operating conditions for at least one of desalination equipment and fluid injection equipment to be used in a low salinity waterflood on a hydrocarbon-bearing reservoir. In particular this invention relates to systems and methods to be used when the reservoir comprises relatively permeable layers interbedded with relatively impermeable layers and where the relatively impermeable layers have a relatively high concentration of ions compared to that of the relatively permeable layers when the low salinity water is present therein.

Background of the Invention

A hydrocarbon-bearing reservoir typically takes the form of a plurality of sandstone layers interbedded with shale layers. The sandstone layers have sufficient porosity and permeability to store and transmit fluids (for example oil and water). Typically the oil is held in pores of the rock formation. By contrast the shale layers are relatively impermeable to these fluids.

It is known that only a portion of the total crude oil present in a reservoir can be recovered during a primary recovery process, this primary process resulting in oil being recovered under the natural energy of the reservoir. Secondary recovery techniques are therefore often used to force additional oil out of the reservoir. One example of a secondary recovery technique is to directly replace the oil with a displacement fluid (also referred to as an injection fluid), usually water or gas.

Enhanced oil recovery (EOR) techniques may also be used. The purpose of such EOR techniques is not only to restore or maintain reservoir pressure (as is done by typical secondary recovery techniques), but also to improve the displacement of the oil from the reservoir, thereby maximizing the recovery of oil from the reservoir and minimizing the residual oil saturation of the reservoir (the volume of oil present in the reservoir).

"Waterflooding" is one of the most successful and extensively used secondary recovery methods. Water is injected, under pressure, into reservoir rock layers via injection wells. The injected water acts to help maintain reservoir pressure, and sweeps the displaced oil ahead of it through the rock towards production wells from which the oil is recovered. The water used in waterflooding is generally saline water from a natural source (such as seawater) or may be produced water (i.e. water that is separated from the crude oil at a production facility).

In addition to waterflooding using saline water, it is possible to use lower salinity injection water (for example, brackish water such as estuarine water, or fresh water such as river water, or lake water). The use of low salinity waterflooding can increase the amount of oil recovered compared to that recovered using high salinity water since the low salinity water is better able to displace the oil from the reservoir.

The water used in a low salinity waterflood typically has a total dissolved solids (TDS) content in the range of 500 to 12,000 ppm. It is also preferred that the ratio of the total multivalent cation content of the low salinity injection water to the multivalent cation content of the formation water that is present in the sandstone layers of the reservoir is less than 1. The use of a low salinity waterflood is particularly beneficial when oil that is present in the sandstone layers of the reservoir (typically oil that is adhering to the surface of the sandstone rock) is a medium or light crude having an American Petroleum Institute (API) gravity of at least 15° C., preferably at least 20° C., and for example an API gravity in the range of 20° C. to 60° C.

During a low salinity waterflood, the low salinity injection water is injected into and flows through the sandstone layers of the reservoir. By contrast, little water flows through the relatively impermeable shale layers. Thus, the oil is produced from the high permeability sandstone layers while insignificant amounts of oil are produced from the low permeability shale layers. Indeed, shale is often so impermeable that the interbedded shale layers of the reservoir remain unsaturated with oil during migration of oil from a source rock into the sandstone layers of the reservoir. Instead, the shale layers are saturated with connate water that is typically of high salinity.

It has now been found that for reservoirs having interbedded sandstone and shale layers, the incremental oil recovery effect that is achieved using low salinity waterflooding may be reduced. This is due to the diffusion of ions from higher salinity connate water present in the pore space of the shale layers into the low salinity water that is flowing through the adjacent sandstone layer of the reservoir. This reduction in recovery is of particular concern when large volumes of high salinity connate water reside in shale layers that are interbedded with the sandstone layers of the reservoir and when the interbedded sandstone layers are relatively thin.

The dominant mass transfer mechanism from the connate water of the shale layers to low salinity water that is flowing through the adjacent sandstone layers of a reservoir is molecular diffusion, whereby salt ions diffuse from the connate water in the shale layer to the low salinity water in the sandstone layer. Typically, the molecular diffusion of salt ions from the shale layer occurs in a direction substantially orthogonal to the direction of flow of the low salinity water through the adjacent sandstone layer (i.e. in the direction of the concentration gradient).

The diffusion of the salt ions from higher salinity connate water present in the pore space of the shale layers can reduce the effectiveness of a low salinity waterflood by increasing the salinity of the water flowing through the sandstone layers. It is therefore an object of the invention to determine the effectiveness of low salinity waterflooding and to consequently configure operating conditions of desalination equipment and/or fluid injection equipment to be used in the low salinity waterflooding.

BRIEF SUMMARY OF THE DISCLOSURE

In accordance with at least one embodiment of the invention, methods, devices, systems and software are provided for configuring equipment for use in a low salinity waterflood. This is achieved by a combination of features recited in each independent claim. Accordingly, dependent claims prescribe further detailed implementations of the present invention.

According to a first aspect of the invention there is provided a computer-implemented method for configuring operating conditions for at least one of desalination equipment and fluid injection equipment to be used in a low salinity waterflood on a hydrocarbon-bearing reservoir, wherein the reservoir comprises relatively permeable layers interbedded with relatively impermeable layers and is penetrable by an injection well and a production well, the low salinity waterflood comprising injecting low salinity water into the hydrocarbon-bearing reservoir from the injection well whereby to pass through the relatively permeable layers of the reservoir from the injection well to the production well, and wherein the relatively impermeable layers have a relatively high concentration of ions compared to that of the relatively permeable layers when the low salinity water is present therein, the method comprising configuring at least one processor and at least one memory including computer program code to cause the processor to:

derive an ion diffusion distance value from: a diffusion coefficient indicative of a rate of diffusion of ions through the relatively permeable layers when the low salinity water is present therein; and a residence time value indicative of the time required for the low salinity water to pass from the injection well to the production well through the reservoir;

compare the thickness of the relatively permeable layers to the derived ion diffusion distance value;

generate, based on a result of the comparison, an indication of the effectiveness of performing a low salinity waterflood; and configure, based on the indication of the effectiveness, operating conditions for at least one of desalination equipment and fluid injection equipment to be used in said low salinity waterflood.

The present invention also provides a computer readable storage medium storing computer readable instructions thereon for execution on a computing system to implement the above method.

Performing a low salinity waterflood requires, amongst other things, a significant quantity of low salinity water, which is generally not available in abundance. This means that it is important to be able to determine a measure of how effective the low salinity waterflood will be. Such a determination may be made by performing a fine scale reservoir simulation; however this requires a large amount of computing resources to perform, typically many hours of processing using a mainframe or 'supercomputer'. By deriving the ion diffusion distance value and comparing this to the thickness of the layers in the reservoir, an indication of the effectiveness of performing a low salinity waterflood can be generated using significantly reduced computing resources. The indication can be used to configure the operating conditions of desalination equipment and/or fluid injection equipment in order to ensure that any low salinity waterfloods performed are as effective as possible, and therefore that the limited supply of low salinity water is used to maximum effect.

A decision on whether to implement a low salinity waterflood will often be taken early on in the reservoir planning or development, so the indication of the effectiveness of performing the low salinity waterflood that is generated can be used to determine operating conditions, such as instructions relating to installation, injection and production, of fluid injection equipment and/or desalination equipment. Hypothetical values and/or measurements, which are made upon initial appraisal of a reservoir or rock formation at an initial or early stage of oilfield planning, are used to determine operating conditions of the injection and/or desalination equipment before installation or drilling take place. This saves time, effort and technical resources by avoiding any need to retro-fit such equipment on an ad-hoc basis once drilling or even oil recovery have begun.

It requires significant time and resources to drill a well in an oilfield, therefore it is desirable to ensure that the maximum distance is present between wells. However, there are disadvantages of having such a large distance, one of which is that, should a low salinity waterflood be performed, the effectiveness will reduce with increasing interwell distance. The present invention allows for hypothetical values to be used in configuring the operating conditions of the equipment; for example, a hypothetical inter-well distance and hypothetical superficial velocity of the low salinity water through the relatively permeable layers can be used in generating the indication of the effectiveness of the waterflood. The hypothetical interwell distance is based on potential well locations identified during an initial reservoir appraisal (together with measurement data from the reservoir, if required). Should the generated indication of the effectiveness confirm that a sufficiently effective low salinity waterflood is likely to result, the potential well locations can be confirmed as being acceptable. Similarly, the position of an infill well can be determined and optimised, for example after commencement of the low salinity waterflood. In an offshore environment, there may be relatively few injection wells and production wells, so the placement of these wells is of great importance.

According to further aspects of the invention there are provided systems and apparatuses for performing the methods described above and computer readable storage media storing computer readable instructions thereon for execution on a computing system to implement the methods described above.

Further features and advantages of the invention will become apparent from the following description of preferred embodiments of the invention, given by way of example only, which is made with reference to the accompanying drawings.

BRIEF DESCRIPTION OF THE DRAWINGS

Systems and methods will now be described as embodiments of the present invention, by way of example only, with reference to the accompanying figures in which.

DETAILED DESCRIPTION OF ILLUSTRATIVE EMBODIMENTS OF THE INVENTION

Figure 1:
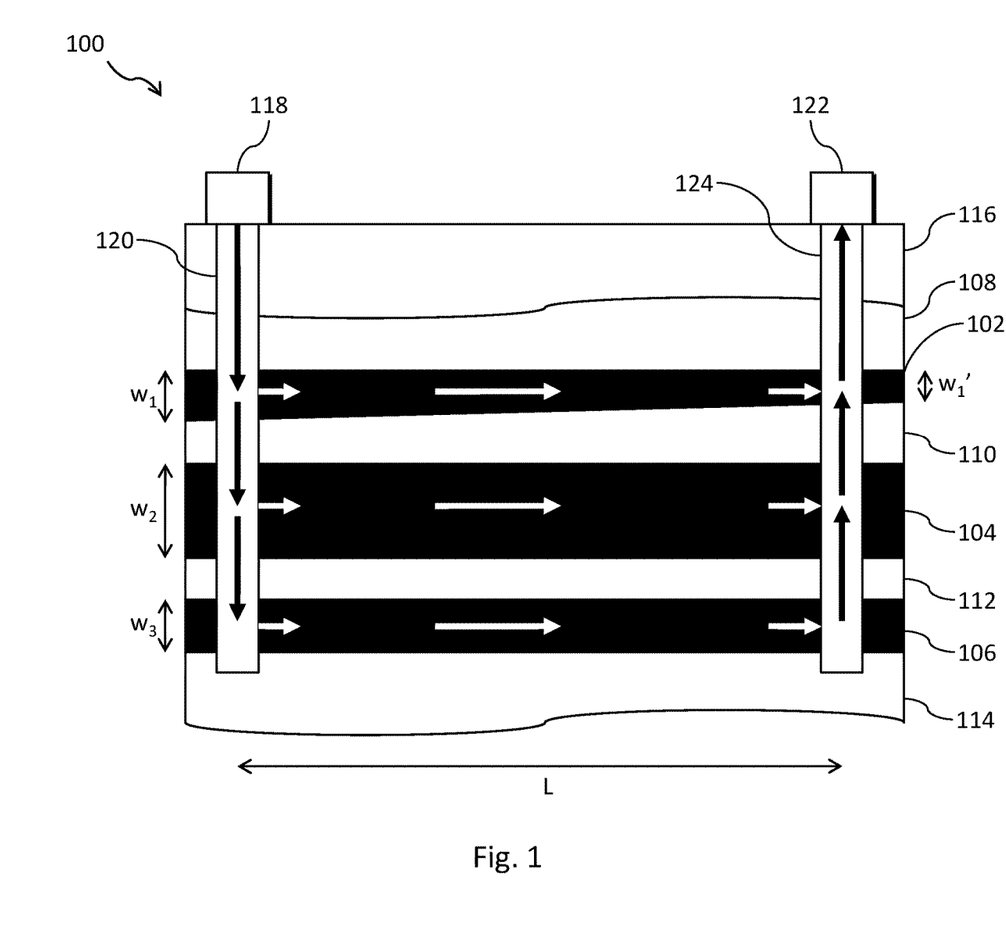
FIG. 1 shows a schematic diagram of an oil recovery system and a reservoir in respect of which embodiments of the invention are applicable.

FIG. 1 is a schematic block diagram showing a simplified representation of a crude oil recovery system 100. Within the system a multi-layer reservoir is present. In this example, the reservoir comprises a series of interbedded permeable and impermeable layers. The permeable layers (in this example sandstone) bear oil in the pore spaces within the rock, and are referenced 102, 104 and 106. The impermeable layers (in this example shale) generally do not bear oil, and are referenced 108, 110, 112 and 114. Above the top impermeable layer 108 is shown a generalized surface layer 116 which may comprise multiple, non-oil bearing layers, and (if the reservoir is offshore) a layer of seawater. The composition of these layers is not relevant to this example.

The permeable and impermeable layers make up the reservoir. Penetrating the reservoir is an injection well, comprising a control station 118 and a well bore 120; and a production well, comprising a control station 122 and a well bore 124. The injection and production wells are separated by a distance L as shown. Typically there are many more wells than the two shown here; however two are shown in this exemplary embodiment for simplicity. It should be appreciated that during initial appraisal of the reservoir and the planning stages of the oilfield, the well locations are potential well locations and their interwell distances are hypothetical, calculated based on the various potential well locations.

Each of the permeable layers (102, 104 and 106) in the reservoir has an associated thickness ($w_1$, $w_2$ and $w_3$ respectively). As can be seen from the figure, each layer has a different thickness. In addition, it can be seen that layer 102 has a varying thickness, being of thickness $w_1$ at the injection well end, and of a narrower thickness $w_1'$ at the production well end. This change in thickness will be referred to later.

When in use for a low salinity waterflood, fluid injection equipment injects low salinity water as an injection fluid under pressure into the reservoir via the injection well. The low salinity water flows along each of the permeable layers 102, 104 and 106 as shown by the arrows. The low salinity water forces the oil in the reservoir ahead of it causing the oil to be forced from the reservoir into the well bore of the production well (again shown by the arrows). From there, the pressure of the reservoir, optionally aided by pumps located in the well bore of the production well, lifts the oil and water received from the reservoir up to the surface where it can be stored, refined and used.

The fluid injection equipment typically comprises injection pumps, a main injection line, manifolds and dedicated injection lines leading from the manifolds to the injection well(s). Optionally, the injection equipment includes an injection line for a high salinity water such as a produced water or seawater (which are used as drive fluids).

During a low salinity waterflood, the low salinity injection water may be passed continuously into the injection well and into the sandstone layers of a reservoir by the injection equipment. However, it is preferred that the low salinity injection water is passed in one or more portions (hereinafter referred to as "slugs") of a controlled volume, which is normally expressed in terms of the "pore volume" or PV. The term "pore volume" is used herein to mean the volume of the pore space in the sandstone rock layers between an injection well and a production well and may be readily determined by methods known to the person skilled in the art. Such methods may include measuring the time taken for a tracer to pass through the sandstone layers from the injection well to the production well (again, in a "pre-drilling" scenario, this may be a hypothetical value). In the case of physical wells, the swept volume is the actual volume swept by the injection water averaged over all flow paths between the injection well location and the production well location, while in the case of simulated wells, the swept volume is the hypothetical volume swept by the injection water averaged over all flow paths between a given potential injection well location and a given potential production well location.

Although, it is possible to continue to inject the low salinity injection water into the reservoir, typically the pore volume of the slug of low salinity injection water is minimized since there may be limited injection capacity for the low salinity injection water owing to the need to dispose of produced saline water (which is disposed of by injection into the reservoir). Thus, the volume of the slug of low salinity injection water is preferably less than 1, and may for example be less than 0.5 PV. Therefore, the slug of low salinity injection water may have a pore volume in the range of 0.2-0.9 PV, and more preferably may be in the range of 0.3-0.45 PV.

After injection of a slug of low salinity injection water, a drive (or post-flush) water of higher multivalent cation content and/or higher TDS (i.e. high salinity), may be injected into the reservoir. For example, the drive water may have a total dissolved solids (TDS) of at least 30,000 ppm, for example, 30,000 to 50,000 ppm and a multivalent cation content of at least 350 ppm. By contrast the water in the low salinity slug typically has a TDS content in the range of 500 to 12,000 ppm. Such a low salinity slug may have a multivalent cation content of less than 40 ppm.

The volume of the slug of low salinity injection water may be small yet the slug is still capable of releasing substantially all of the oil that can be displaced from the surface of the pores of the sandstone rock under the reservoir conditions. Generally, the volume of the slug of low salinity injection water is at least 0.2 PV, as a slug of lower volume tends to dissipate in the sandstone rock and may not result in appreciable incremental oil production. It has also been found that where the volume of the low salinity injection water is at least 0.3 PV (and preferably at least 0.4 PV), the slug tends to maintain its integrity within a sandstone rock (that is, it does not disperse within the rock) and therefore continues to sweep displaced oil towards a production well. Thus, the incremental oil recovery for a reservoir that comprises sandstone layers approaches a maximum value with a slug of at least 0.3-0.4 PV. There is little additional incremental oil recovery with higher volume slugs.

Where the slug of low salinity injection water has a volume of less than 1 PV (that is the low salinity slug will not fill the reservoir, and will need to have a driving injection fluid, typically high salinity water, injected behind it), the drive water will ensure that the fractional pore volume slug of low salinity water (and hence the released oil) is swept through the reservoir to the production well. In addition, the injection of the drive water may be required to maintain the pressure in the reservoir. Typically, the drive water has a greater volume than the slug of low salinity injection water.

Although the slug of low salinity water that is injected into the oil-bearing sandstone layers of the reservoir is only a fraction of the pore volume, the slug generally remains intact within the formation and continues to sweep displaced oil towards a production well. Without wishing to be bound by any theory, it is believed that although there is dispersive (diffusive) mixing between the higher salinity drive water and the low salinity water at the tail (back) of the slug there is little dispersive (diffusive) mixing between the low salinity water and the formation water at the front of the slug. The reason why there is little diffusive mixing between the low salinity water and the formation water at the front of the slug is that there is an ion exchange reaction occurring between the monovalent cations in the low salinity water slug and the multivalent cations (predominantly divalent cations) that are binding the residual oil to the rock surface. This means that the slug attains a steady state arising from the fact that the velocities of the ion concentrations are lower in the leading edge than in the trailing portions (because of ion exchange driven adsorption at the leading edge), and thus the slug sharpens on propagation. In mathematical terms, this arises because the diffusion equation for mixing of the low salinity water with the formation water that is present in the sandstone layers (which has diffusion terms for the concentrations of the individual ions in the low salinity water and the individual ions in the formation water that are dependent upon distance and time) is balanced by the addition of an extra mathematical term that takes into account ion exchange between the low salinity water and the rock (sorption). For these reasons, the slug of low salinity water remains intact (does not substantially mix with the formation water) as the slug is forced through the sandstone layers by the subsequently injected higher salinity drive water.

During a low salinity waterflood, the extent of diffusion of ions from the high salinity water trapped in the impermeable layers into the low salinity water, and hence the impact of the resulting increase in salinity of the injected low salinity water on the incremental oil recovery is dependent upon one or more of the following parameters:

1. the flow rate of the low salinity water through the permeable (sandstone) layers of the oil reservoir (generally expressed as a superficial velocity, v);
2. the interwell distance, L, between the injection well that is used to inject the low salinity water into the oil reservoir and the production well that is used to produce oil from the oil reservoir;
3. salt diffusion coefficients in the impermeable (shale) layers;
4. the concentration gradient between the dissolved salts that are present in the connate water of a shale layer and the dissolved salts that are present in the low salinity water that is flowing through the adjacent sandstone layer;
5. the thickness of the interbedded shale layers of the oil reservoir;
6. the thickness of the interbedded sandstone layers of the oil reservoir;
7. the fraction of the total sandstone reservoir made of thin interbedded and hydraulically connected sandstone layers within a reservoir.

The flow rate (v) and the interwell distance (L) define the 'residence time', t, of the low-salinity water in the sandstone layer(s) of the reservoir and therefore the time available for salt ions to diffuse from a shale layer into the low salinity water that is flowing through an adjacent sandstone layer of the reservoir. Thus, the residence time, t, may be defined as L/v wherein L is the interwell distance between the injection and production wells and v is the superficial velocity of the low salinity water in the sandstone layers of the reservoir. If the residence time of the low salinity water in the sandstone layer of the oil reservoir is low, there may be little salt diffusion from the shale layer into the low salinity water and hence an insignificant increase in the total dissolved solids (TDS) content of the low salinity water and/or its multivalent cation concentration. Conversely, if the residence time of the low salinity water in the reservoir is high, there may be significant salt diffusion into the low salinity water and a significant increase in TDS content of the low salinity water and/or its multivalent cation concentration.

As discussed above, the flow rate of the low salinity water through the sandstone layers of the reservoir may be expressed as a superficial velocity, v, which is defined as the volumetric flow rate of the low salinity water through the sandstone layers of the reservoir (which can be determined from the volumetric injection rate) divided by the cross-sectional area of the sandstone layers. As an approximation, the superficial velocity corresponds to the frontal advance rate of the low salinity water in the reservoir.

The superficial velocity of the low salinity water in the sandstone layers of a reservoir is typically in the range of 0.05 to 5 feet/day (0.015 to 1.5 meters/day) and more often is in the range of 1 to 4 feet per day (0.3 to 1.2 meters/day). However, as discussed below, the superficial velocity may be limited by the permeability of the sandstone rock or the injectivity of the reservoir.

The interbedded sandstone layers of a reservoir may be isolated from one another such that there is a single flow path for the low salinity water through each sandstone layer from the injection well to the production well. Alternatively, the sandstone layers of a reservoir may be hydraulically interconnected owing to fractures or faults in the shale layers or to the shale layers not being contiguous with the sand layers along the entire interwell distance between the injection well and the production well. In this situation, the low salinity injection water finds many flow paths through the hydraulically connected sandstone layers of the reservoir and it is the average superficial velocity of the low salinity water through the sandstone layers that is determined.

Typically, each of the sandstone layers of the reservoir has a permeability of at least 1 millidarcy, and more often at least 500 millidarcies. Generally, the permeability of each of the sandstone layers of the reservoir is in the range of 1 to 1000 millidarcies. The permeability of the interbedded sandstone layers of the reservoir may be determined, for example, from measurements made on core samples taken from the reservoir using standard techniques. The superficial velocity for the low salinity water may vary with varying permeability of the sandstone rock.

The superficial velocity of the low salinity water through the sandstone layers of the reservoir may also be dependent upon the injectivity of the reservoir. The injectivity of the reservoir refers to the rate and pressure at which injection fluids can be injected into a reservoir from an injection well without hydraulically fracturing the reservoir. Thus, the pressure in the injection well should be above the reservoir pressure but below the pressure at which fractures start to be induced in the reservoir rock. The fracture induction pressure will be reservoir specific and can be readily determined using techniques well known to the person skilled in the art.

Depending on the reservoir pressure and the fracture induction pressure, the injection pressure of the low salinity water may be in the range of 6,500 to 150,000 kPa absolute, and more specifically, 10,000 to 100,000 kPa absolute (100 to 1000 bar absolute). Thus, the superficial velocity for the low salinity water may be increased by increasing the injection pressure and hence the rate at which the low salinity water is injected into the reservoir.

In the example system shown in FIG. 1 there is only one injection well and one production well; however, in other embodiments there may be more than one injection well and more than one production well in the reservoir. The wells may be located on land or may be located offshore.

On land, there may be many different spatial arrangements between the injection wells and production wells of a reservoir. For example, injection wells may be located around a production well. Alternatively the injection wells may be in two or more rows between each of which are located production wells. However, irrespective of the spatial arrangements of the wells it is generally the case that the interwell distance L between any injection well and its associated production well(s) is less than 3000 feet. Typically, the interwell distance is in the range of 1000 to 2000 feet. Decreasing the interwell distance L between an injection well and its associated production wells reduces the residence time of the low salinity water in the sandstone layers of the reservoir.

Offshore, there are typically fewer production wells and injection wells resulting in a larger interwell distance L of, for example, 3000 feet thereby reducing the ability of an operator to control the residence time t of the low salinity water in the sandstone layers of the reservoir. Accordingly, it may be necessary to select a reservoir for a low salinity waterflood dependent upon one or more of the other parameters listed above.

Embodiments of the invention provide computer systems, and computer implemented methods which may be used to assist in the performing of a low salinity waterflood as described above with reference to FIG. 1. To do this, embodiments of the invention may include a computer system running low salinity waterflooding (LSW) software components which enable the system to generate an indication of the effectiveness of performing a low salinity waterflood in the reservoir, and based on the effectiveness determined, to configure operating conditions for desalination equipment and/or fluid injection equipment, which can then be used in the low salinity waterflood. Therefore, the system allows for efficient planning and control of a low salinity waterflood. The effectiveness indicated can be used to determine operating conditions for equipment, for example, if it is deemed effective, an instruction to install the desalination equipment in the oilfield facilities; further examples of operating conditions will be discussed below.

The computer system may be located in a planning and control centre (which may be located a substantial distance from the reservoir, including in a different country). Alternatively, the computer system may be part of the control systems of the reservoir, such as control stations 118 and 122 as shown in FIG. 1. The LSW software components may comprise one or more applications as are known in the art, and/or may comprise one or more add-on modules for existing software.

A schematic block diagram showing such a computer system will now be described with reference to FIG. 2. The computer system 200 comprises a processing unit 202 having a processor, or CPU, 204 which is connected to a volatile memory (i.e. RAM) 206 and a non-volatile memory (such as a hard drive) 208. The LSW software components 209, carrying instructions for implementing embodiments of the invention, may be stored on the non-volatile memory 208. In addition, CPU 204 is connected to a user interface 210 and a network interface 212. The network interface 212 may be a wired or wireless interface and is connected to a network, represented by cloud 214. Thus the processing unit 202 may be connected with sensors, databases and other sources and receivers of data through the network 214.

In use, and in accordance with standard procedures, the processor 204 retrieves and executes the LSW software components 209 stored in the non-volatile memory 208. During the execution of the LSW software components 209 (that is when the computer system is performing the actions described above) the processor may store data temporarily in the volatile memory 206. The processor 204 may also receive data (as described in more detail below), through user interface 210 and network interface 212, as required to implement embodiments of the invention. For example, data may be entered by a user through the user interface 210 and/or received from e.g. a remote sensor in a production well through the network 214 and/or may be retrieved from a remote database through the network 214.

These data may be generated and/or stored in a number of ways known to the skilled person. For example, diffusion coefficients (described below) may be determined in a laboratory from a core sample relating to the reservoir (using well known processes). Once determined, this data may be actively sent to the processing unit 202, or stored in a database to be retrieved as required by the processing unit 202. Values such as an interwell distance value and superficial velocity may be hypothetical values, based on potential injection, production or infill well locations. Further alternatives will be readily apparent to the skilled person.

Having processed the data, the processor 204 may provide equipment operating conditions in the form of an output via either of the user interface 210 or the network interface 212. If required, the output may be transmitted over the network to remote stations, such as a planning centre or the control station 118, 122 for fluid injection equipment or desalination equipment. Such processes will be readily apparent to the skilled person and will therefore not be described in detail.

Examples of the computer implemented methods by which the computer system described above may operate to implement embodiments of the invention will be described below; however, to put these methods into context, we will now describe some background information relating to the diffusion of ions into low salinity water flowing through a reservoir.

Ions (for example salt ions) may diffuse from a shale layer into an adjacent interbedded sandstone layer relatively slowly, compared to a typical residence time t for the low salinity water in the sandstone layers of the reservoir. Consequently, the concentration gradient, and therefore the direction of the diffusion in the layers can be considered to be substantially perpendicular to the shale-sandstone boundary, and, as such, the diffusion can be considered to be one dimensional.

In addition, the shale layers can be considered to be of sufficient size, and to have a sufficiently high concentration of ions that they can be modelled as an unlimited source of ions. To put this another way, the slug of low salinity water represents only a small fraction of the volume of the connate water in the shale layers. A consequence of this is that the concentration of ions at the boundary between the shale and sandstone can be considered to be constant.

However, in some cases the thickness of the interbedded shale layers may be of significance as this determines the total amount of salt ions available for diffusion from an interbedded shale layer into the low salinity water that is flowing through an adjacent sandstone layer. In reservoirs having relatively thin interbedded shale layers, the amount of salt ions available for diffusion into the interbedded sandstone layers may be low. Therefore, in alternative embodiments it is envisaged that the thickness of the shale layers may be taken into account in the calculations disclosed herein, insofar as thin shale layers can no longer be approximated as an unlimited supply of ions.

Finally, the sandstone layer can be considered a semi-infinite medium; that is, the portion of the layer concerned is bounded on one side by the shale, but extends to infinity from there. This is an approximation, since the sandstone layer will be bounded on the other side (most likely by another shale layer), however it is valid for the examples given.

An analytic expression for the one dimensional diffusion of ions from a constant composition source into a semi-infinite porous medium of low permeability (e.g. from the shale to the sandstone rock) is given by the following one dimensional solution to Fick's law:

$$\frac{C(z)}{C_0} = \mathrm{erfc}\left[\frac{z}{2\sqrt{D_a t}}\right] \quad \text{(Equation 1)}$$

where z is distance (depth) within the sandstone measured from the boundary surface of the sandstone and the shale, $C_0$ is the concentration of the ion at z=0 (i.e. the concentration in the shale layer), $D_a$ is the "apparent diffusion coefficient" which defines the rate of diffusion of the ions through the sandstone, t is time and C(z) is the concentration of the diffusing ion in the porous medium at a depth of z. The skilled person will recognize that there are a number of different types of diffusion coefficient which might be used. For example: a bulk diffusion coefficient relates to the diffusion of ions in a bulk liquid; a pore diffusion coefficient takes into account the tortuosity of the pores in the sandstone which constrain the diffusion; finally the apparent diffusion coefficient takes into account both tortuosity and sorption of ions. For a non-sorbing ion, the pore diffusion coefficient is the same as the apparent diffusion coefficient, however this is not the case for a sorbing ion. The skilled person will therefore understand that any appropriate diffusion coefficient may be used in embodiments of the invention without departing from the scope of the claims.

Equally, the above described methods are related to salt ions which are non-sorbant in sandstone. However it will be apparent to the skilled person that the invention may be adapted to ions which are sorbant in sandstone (with appropriate adaptation of the diffusion coefficient).

The salt diffusivities in shale can be determined experimentally with a sufficient degree of accuracy to determine the effect of salt diffusion on the incremental oil recovery that can be achieved with a low salinity waterflood. Since the rate of salt diffusion is proportional to the concentration gradient between the high salinity connate water contained in the pore space of the shale layer and the low salinity water that is flowing through the pore space of an adjacent sandstone layer, it is important to determine the salinity of the connate water that is present in the shale layers together with the concentrations of the individual ionic (salt) species in this connate water, in particular, the concentration of the various multivalent cations together with the total concentration of multivalent cations in this connate water.

Consequently, samples of the connate water that is present in the pore space of the sandstone layers and in the pore space of the interbedded shale layers may be obtained by taking a core sample from the reservoir through the different reservoir layers. From these the TDS and multivalent cation content of the water contained within the different layers of the core may then be determined.

The low salinity water that is injected into the sandstone layers of the oil reservoir may have a total dissolved solids (TDS) content in the range of 200 to 12,000 ppm, preferably, 500 to 10,000 ppm. Where the formation rock contains swelling clays, in particular, smectite clays, a relatively high TDS for the low salinity water is required in order to stabilize the clays, thereby avoiding the risk of formation damage. Thus, where the formation rock contains an amount of swelling clays sufficient to result in formation damage, the low salinity water that is injected into the oil-bearing formation preferably has a TDS content in the range of 8,000 to 12,000 ppm. Where the formation comprises amounts of swelling clays that do not result in formation damage, the TDS content of the low salinity water is typically in the range of 200 to 8,000 ppm, preferably 500 to 8,000 ppm, and for example may be 1,000 to 5,000 ppm. In this context, it is observed that an overall increase in the salinity of the low salinity water may be tolerated provided that the salinity of the low salinity water remains within the desired range for the low salinity waterflood.

The concentration gradient between the connate water that is present in the shale layer and the low salinity injection water that is flowing through an adjacent sandstone layer is particularly significant when the connate water of the shale layer has a TDS of at least 100,000 ppm, especially, at least 200,000 ppm, for example, is in the range of 150,000 to 400,000 ppm, in particular, 150,000 to 250,000 ppm.

The incremental oil recovery that is achieved for a low salinity waterflood is dependent upon the ratio of the total multivalent cation content in the low salinity injection water that is injected into the sandstone layers of the reservoir to the total multivalent cation content in the connate water that is present in the pore space of the sandstone layers of the reservoir (hereinafter "multivalent cation ratio"). It has previously been found that this multivalent cation ratio should be less than 1, for example, less than 0.9. Generally, the lower the multivalent cation ratio the greater the amount of oil that is recovered from the reservoir. Thus, the multivalent cation ratio is preferably less than 0.8, more preferably, less than 0.6, yet more preferably, less than 0.5, and especially less than 0.4 or less than 0.25. The multivalent cation ratio may be at least 0.001, preferably, at least 0.01, most preferably, at least 0.05, in particular at least 0.1. Preferred ranges for the multivalent cation ratio are 0.01 to 0.9, 0.05 to 0.8, but especially 0.05 to 0.6 or 0.1 to 0.5. The ratio of the total divalent cation content of the said low salinity injection water to the total divalent cation content of the formation water that is present in the sand layers of the reservoir (hereinafter "divalent cation ratio") should also less than 1. The preferred values and ranges for the multivalent cation ratio may be applied mutatis mutandis to the divalent cation ratio.

Typically, the calcium content of the low salinity injection water is in the range of 1 to 100 ppm, preferably 5 to 50 ppm. Typically, the magnesium content of the low salinity injection water is in the range of 5 to 100, preferably 5 to 30 ppm.

The barium content of the low salinity injection water may be in the range of 0.1 to 20, such as 1 to 10 ppm. Typically, the total content of multivalent cation in the low salinity injection water is 1 to 200 ppm, preferably 3 to 100, especially 5 to 50 ppm with the proviso that the multivalent cation ratio is less than 1.

Accordingly, diffusion of multivalent cations from the connate water contained in the pore space of a shale layer into the low salinity water that is flowing through an adjacent sandstone layer of the reservoir is of concern if this results in an increase the "multivalent cation ratio" or the "divalent cation ratio" to above 1.

Typically, the multivalent cation content of the connate water that is contained in the pore space of the shale layer is in the range of 7,500 to 50,000 ppm, in particular, 10,000 to 30,000 ppm, with higher multivalent cation concentrations being associated with higher salinity connate waters.

The apparent diffusivities of non-sorbing ions in sandstone rock may be determined using the following methodology. In sandstone, the effective diffusivity is:

$$D_e = \frac{D_0 \phi}{F \phi^{1-m}} = D_0 \cdot \phi^m$$

wherein $D_0$ is the bulk diffusivity in aqueous solution, $\phi$ is the porosity of the sandstone rock, m is the Archie 'cementation factor', and F is the formation resistance factor. For a typical sandstone rock, the cementation factor, m, lies within the range of 1.7 to 2.7. If $D_0$ is taken to be $3.1 \times 10^{-9}$ m$^2$/s (this is the value for the harmonic mean of bulk diffusivity of Na$^+$ and Cl$^-$ ions at a temperature of 132.8° F.), then for a sandstone rock having a porosity of 0.3, the effective diffusivity, $D_e$, lies within the range of $1 \times 10^{-10}$ to $4 \times 10^{-10}$ m$^2$/s for the stated range of m. Accordingly, the apparent diffusivity, $D_a = D_0 \cdot \phi^{m-1}$, for a non-sorbing ion (such as Na$^+$ or Cl$^-$) lies within the range of $4 \times 10^{-10}$ to $1.33 \times 10^{-9}$ m$^2$/s for the stated range of m.

The following relationships between the chemical characteristics of the connate water contained in the pore space of the shale layers and the chemical characteristics of the injected low salinity water may have an impact on the incremental oil recovery that is achieved with a low salinity waterflood:
(a) the difference in TDS between the low salinity water that is injected into the sandstone layers of the reservoir and the connate water of an interbedded shale layers;
(b) the difference between the multivalent cation concentration of the low salinity water that is injected into the sandstone layers of the reservoir and the multivalent cation concentration of the connate water of an interbedded shale layer.

Thus, as discussed above, the connate water of the shale layer has both a higher TDS and a higher multivalent cation content than the low salinity water that is injected into the sandstone layers of the reservoir. The above described embodiments of the invention allow for the diffusion of the non-sorbant ions, however these methods may be combined with methods to allow for the effects of TDS in the shale layers.

Figure 3:
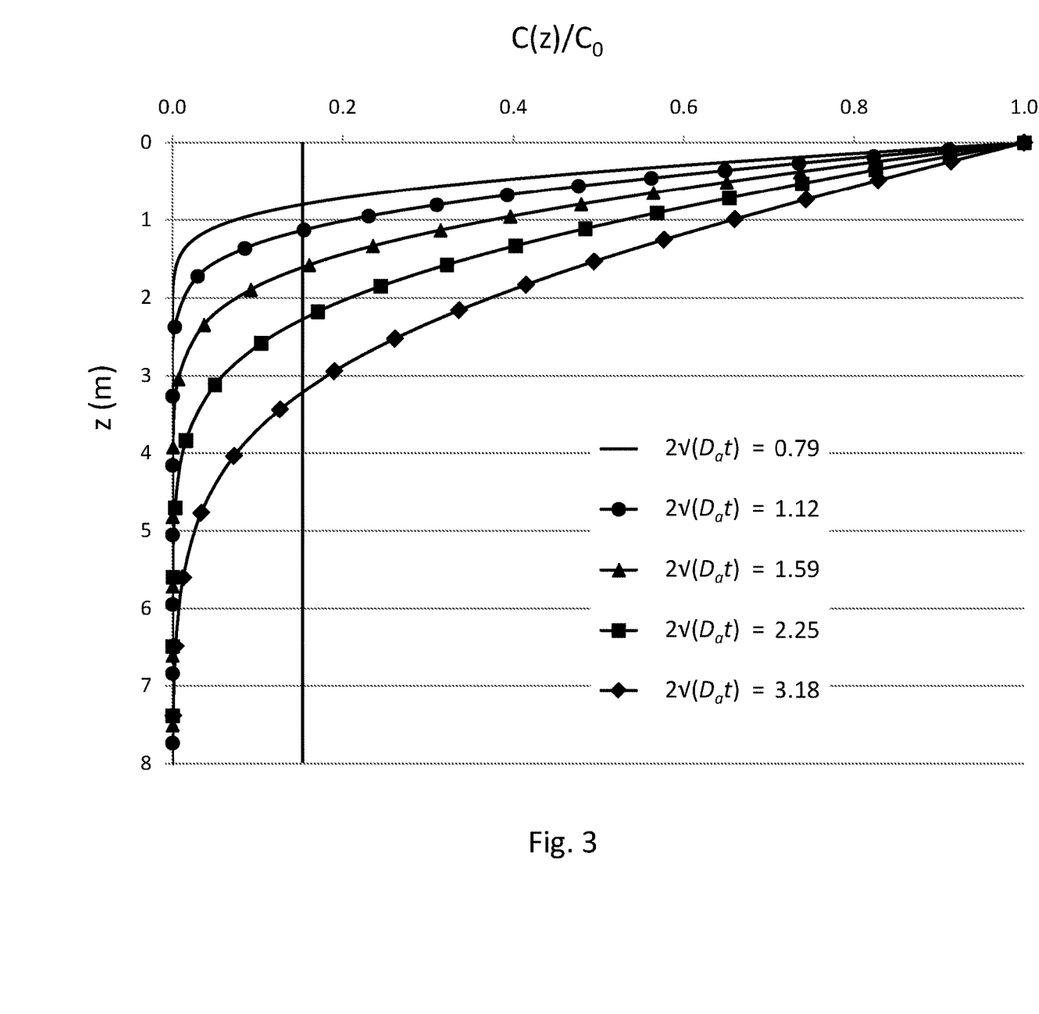
FIG. 3 shows a plot showing the diffusion of ions.

FIG. 3 shows a plot of $C(z)/C_0$ against distance (z). Five lines are shown, each curve being constructed using different values of $2\sqrt{D_a t}$. It can be seen from FIG. 3, the concentration decreases with depth. In addition, the longer the residency time (proportional to L/v), the greater the diffusion.

As can be seen, to minimize the extent of the diffusion, it is desirable to have a short residence time t. As a consequence, it is desirable to use a small interwell distance L and a high superficial velocity v. However, this may be difficult to achieve for both economic and technical reasons. For example, in offshore locations, the cost of drilling additional wells to achieve the desired smaller interwell distances may be prohibitively expensive. To overcome these problems, it is desirable to be able to identify conditions under which a low salinity water flood will be effective, and to determine the effectiveness of any low salinity waterflood that might be performed under such conditions.

Referring to Equation 1, it can be seen that at a value of $z = 2\sqrt{D_a t}$, the concentration ratio ($C/C_0$) has a value of approximately 0.16. Therefore, the distance $d = 2\sqrt{D_a t}$ may be regarded as the "penetration distance" (d), which represents the time-dependent distance within which 87% of the diffusing ions are present. Since the residence time t takes the value of L/v where L and v are the interwell distance and the superficial velocity of the waterflood respectively, the penetration depth d can be rewritten as:

$$d = 2\sqrt{\frac{D_a L}{v}} \quad \text{(Equation 2)}$$

To calculate a measure of the effectiveness of a low salinity waterflood, the penetration depth can be used to calculate a "boundary layer" thickness x. This boundary layer represents the portion of each sandstone layer which is strongly affected by the diffusion of ions into the sandstone layer from the surrounding shale layer. Inside the boundary layer, it is assumed that there is no incremental recovery of the oil (that is, there is no additional recovery of oil from the boundary layer when compared to a high salinity waterflood). Conversely, outside the boundary layer, the diffusion of the ions is assumed to have no effect on the low salinity waterflood.

It will be apparent that the boundary layer increases in thickness as the distance from the injection well increases. The thickness will be effectively zero at the injection well (since there has been no opportunity for the ions to diffuse into the low salinity water). By contrast the thickness of the boundary layer will be at a maximum at the production well. This average thickness of the boundary layer (x) can be calculated from the penetration depth (d) as derived from equation 2 as:

$$x = Ad = 2A\sqrt{\frac{D_a L}{v}} \quad \text{(Equation 3)}$$

In equation 3, the empirical constant A can be varied to tune the equation, $D_a$ and L may be known and relatively constant. The velocity v may be a measure of the superficial velocity through the reservoir; however this is not a requirement, and any appropriate velocity measure may be used. Normally, there will be a boundary layer at the top and bottom of a sandstone layer interbedded between the shale layers.

Typically, A will have a value of 0.5 (assuming the boundary layer grows uniformly from the injection to the production well), however other values may be used. For example, if it is found that a particular reservoir is strongly affected by diffusion of ions, or that the concentration of ions in the shale layers is unusually high, A may be increased to have a value of e.g. 1 or 2. Appropriate values of A may be found empirically by the skilled person, for example by comparing difference simulation results to the results obtained using embodiments of the invention.

The superficial velocity v may be varied by changing the injection pressure, and consequently the value of v to be used in this equation may be varied in dependence on other factors. For example, the maximum superficial velocity which may be used through the reservoir may be limited by, for example, the maximum injection pressure which may be used without hydraulically fracturing the reservoir, or the maximum superficial velocity which may be economically possible. In some embodiments of the invention, the superficial velocity v used in equation 3 may be a predetermined fraction/percentage of the maximum (such as 80% of maximum). Various methods of deriving v will be apparent to the skilled person, and any suitable method may be used within the scope of the invention.

To give an example, if L is 2000 feet, v is 1 foot/day and $D_a$ is $1.33 \times 10^{-9}$ m$^2$/s (an appropriate value for NaCl in sandstone), then if A=0.5, the average boundary layer thickness is approximately 0.5 m (1.5 feet).

The effectiveness of a low salinity waterflood may be calculated using a diffusion degrade factor (F) for the reservoir. The diffusion degrade factor may be generally considered to be a measure of the ratio of the quantity of additional oil recovered when diffusion is taken into account to the quantity of additional oil recovered when diffusion of ions is ignored. The "additional" oil here being the amount of oil recovered by the low salinity waterflood compared to the preceding high salinity waterflood.

One method of calculating this diffusion degrade factor is to compare the total thickness of the non-boundary layers in the reservoir to the total thickness of the sandstone layers overall. Mathematically this can be represented as:

$$F = \frac{\sum (w_n - 2x)}{\sum w_n} \quad \text{(Equation 4)}$$

where, $w_n$ is the thickness of a layer (each layer indexed by n) and x is the average boundary layer thickness calculated above (the coefficient 2 appears because there are two boundary layers per sandstone layer).

Equation 4 simplifies to:

$$F = 1 - \frac{2x}{H} \quad \text{(Equation 5)}$$

where H is the arithmetic mean of the thicknesses of the sandstone layers:

$$H = \frac{1}{n} \sum w_n \quad \text{(Equation 6)}$$

This equation assumes that, within the boundary layers there is no additional oil recovery resulting from low-salinity water flooding, whereas outside the boundary layers, additional oil recovery is unaffected by salt diffusion. Equations 4 and 5 imply a negative contribution to low salinity additional oil recovery in the presence of diffusion when $w_n < 2x$. This may lead to an underestimation of the diffusion degrade factor F. Therefore, Equation 4 may, for example, be modified so that it only applies when $w_n \geq 2x$.

While one method of determining and using a boundary layer thickness has been described above, other possibilities are envisaged without departing from the scope of the invention.

For example, the layers may be categorized as either "marginal facies" or "axial facies". This may be done using the boundary layer thickness. For example, "marginal facies" may denote interbedded sandstone and shale layers where the sandstone layers are strongly affected by diffusion of salt ions, and in view of the above, may be defined as layers having a thickness comparable to, or thinner than, twice the boundary layer thickness x (meaning that the entire sandstone layer is defined as being boundary layer). By contrast, the "axial facies" are interbedded sandstone layers where the sandstone layers are thicker than four times this boundary layer thickness x. The threshold used to categorize these layers (4x above) may take other values, such as 5x or 6x. Having classified the layers, a diffusion degrade factor may then be determined based on the aggregate thickness of the thick (axial) layers to the total thickness of all the layers.

It will be apparent that Equation 5 will tend to underestimate the diffusion degrade factor in cases where there are many layers of a thickness less than twice the boundary layer thickness (since two full boundary layers are assumed to exist for each layer, irrespective of whether the layer is too thin to be able to contain two such layers—and for layers of a thickness less than twice the boundary layer thickness, the boundary layers will effectively be assumed to overlap).

Consequently, the method may be adapted to take this into account. One method by which this may be done is to define an effective non-boundary thickness ($e_n$) for each layer which takes into account this overlap, i.e.:

$$e_n = \begin{cases} w_n - 2x & w_n > 4x \\ \frac{w_n^2}{8x} & w_n \leq 4x \end{cases} \quad \text{(Equation 3a)}$$

from $e_n$, the diffusion degrade factor F can be calculated using a modified version of Equation 4 as follows:

$$F = \frac{\sum e_n}{\sum w_n}, \quad \forall n \quad \text{(Equation 4a)}$$

In Equation 4a, the diffusion degrade factor F is therefore the sum of the effective thicknesses divided by the sum of the layer thicknesses.

Figure 4:
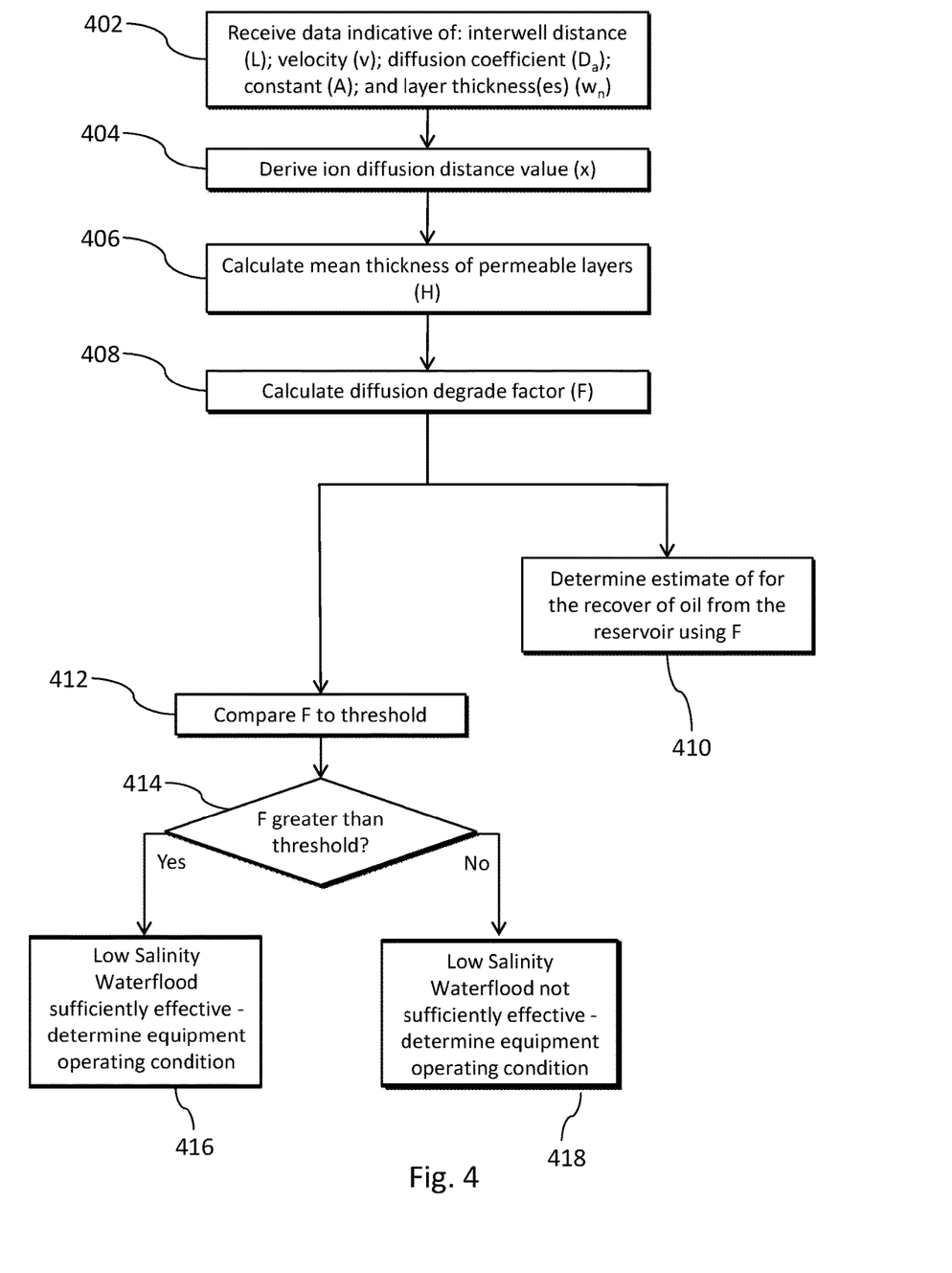
FIG. 4 shows a computer implemented method of determining an indication of the effectiveness of performing a low salinity waterflood and configuring, based on the indication of the effectiveness, operating conditions for at least one of desalination equipment and fluid injection equipment to be used in the low salinity waterflood, according to an embodiment of the invention.

A computer implemented method of determining the effectiveness of performing a low salinity waterflood according to an embodiment of the invention will now be described with reference to FIG. 4. The steps described below may be performed by processor 204 executing the LSW software components 209 as described above with reference to FIG. 2. It will be assumed below that any initialization steps required to initialize the computer system 200, and to retrieve the LSW software components have been performed prior to the start of the method as described from step 402 below.

In step 402 data indicative of values for the interwell distance (L), diffusion coefficient ($D_a$), superficial velocity (v), and the thicknesses ($w_n$) of the sandstone layers in the reservoir is received by the processor. The ion diffusion distance value (x) may be calculated from $D_a$ and t. If this is the case, the processor may, in step 402, receive a value of t instead of the values of L and v.

With reference to FIG. 1, each layer has a thickness $w_n$ where n is an index for the layer (in FIG. 1, there are three layers, therefore n=1, 2 or 3). Moreover, as shown in FIG. 1, layers may have variable thicknesses. Consequently, the thickness data for a layer having a variable thickness may be calculated from, for example, an average thickness of the layer, or from a minimum thickness of the layer (other possibilities may be envisaged by the skilled person).

Figure 2:
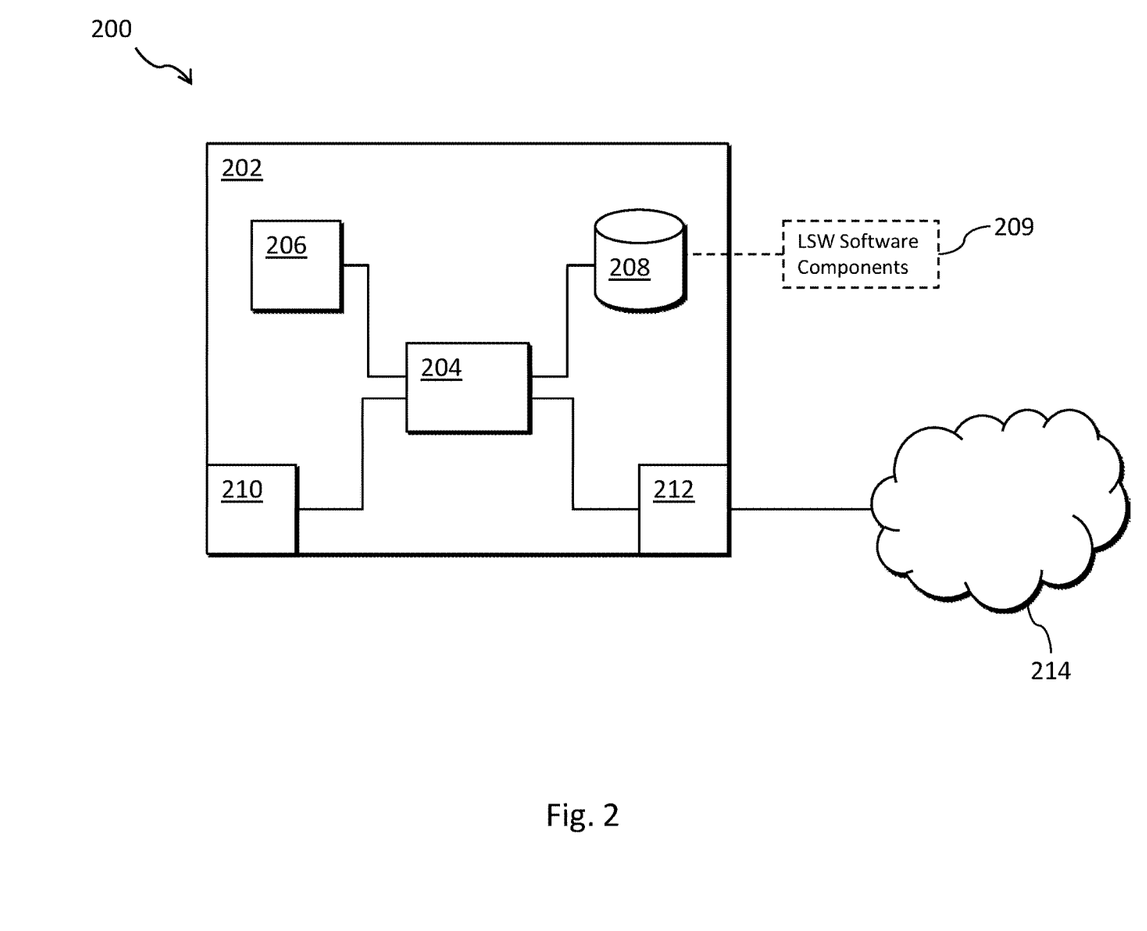
FIG. 2 shows schematic diagram of a processing system in which embodiments of the invention may operate.

The above data may be received through interfaces 210 or 212 as shown in FIG. 2. The data may be provided from a number of sources, including a reservoir model, core samples, database lookup etc. The possible sources of such data will be readily apparent to the skilled person.

In step 404 the processor 204 calculates an ion diffusion distance value (x) from $D_a$, L, v and A. The ion diffusion distance value may, as in this embodiment, be the average boundary layer thickness. Therefore this calculation may be done using Equation 3 shown above, and reproduced here:

$$x = 2A\sqrt{\frac{D_a L}{v}} \quad \text{(Equation 3)}$$

In step 406, the processor 204 calculates the arithmetic mean (represented as H) of the sandstone layers using Equation 6, reproduced here:

$$H = \frac{1}{n}\sum w_n \quad \text{(Equation 6)}$$

While the processor 204 is described as calculating the average (mean) layer thickness (H) for the reservoir, from the individual layer thickness, it will be readily apparent that this value may be directly provided to the processor.

In step 408 the processor 204 calculates a diffusion degrade factor (F) from H and x using Equation 5, reproduced here:

$$F = 1 - \frac{2x}{H} \quad \text{(Equation 5)}$$

As shown in step 410, the diffusion degrade factor F may be used in the generation of an estimate for the recovery of oil from the reservoir. This may be performed by the processor 204, or the diffusion degrade factor F may be provided to a reservoir modelling system to be used in generating estimates of the recovery of oil. One example of this use may be to multiply an estimate of the incremental oil recovery from the low salinity waterflood provided by the model by the diffusion degrade factor F, however alternative methods will be apparent to the skilled person.

One way of determining whether the planned configuration of wells will give rise to a sufficiently effective low salinity waterflood is described in steps 412 to 418. In step 412 the diffusion degrade factor F is compared to a threshold. The threshold may have a predetermined value, which may be, for example, in the range of 0.5 to 0.9. Preferably the threshold has a value in the range of 0.6 to 0.8. Based on the comparison, the system can determine whether a sufficiently effective low salinity waterflood is expected to arise.

Therefore, in step 414, it is determined whether F is greater than the threshold value. If F is greater, then this is taken to indicate that the low salinity waterflood will be sufficiently effective to warrant its performance, and the system configures, in step 416, one or more operating conditions for at least one of desalination equipment and fluid injection equipment to be used in the low salinity waterflood. Alternatively, if F is less than the threshold, the low salinity waterflood will not be sufficiently effective. Operating conditions for one or both of the desalination and injection equipment are then configured accordingly in step 418.

Configuring the operating conditions for the fluid injection equipment can comprise instructing the fluid injection equipment to inject one or more particular fluids into one or more particular injection wells; by "particular fluid" is meant one or more of desalinated water (having a particular salinity and a particular multivalent cation content), water produced from the reservoir, and a higher salinity water such as seawater or brackish water.

Configuring the operating conditions can comprise an instruction to start or stop the injection of fluid into one or more injection wells, which could, for example, be made in response to the completion of a separate action.

The configuration can comprise instructing the fluid injection equipment to inject a particular quantity of fluid into one or more injection wells, for example a preferred slug size or a proportion of low salinity injection water in the case of a low supply.

The configuration can include instructing the fluid injection equipment to inject one or more particular fluids into one or more injection wells in a specified order. This could comprise sequential injection, for example, instructing the injection of a low salinity water into injection well A, then into injection well B, and then into injection well C, in which case it is not necessary to stop or finish the injection into one well (e.g. well A) before commencing injection into another well (e.g. wells B and/or C). This is advantageous where, for example, the desalination equipment has a limited capacity for producing the low salinity water. Another scenario which applies here is one in which multiple fluids are injected into a single injection well, for example, a quantity of low salinity water can be injected into well A, followed by the injection of a drive water, such as a produced water or seawater, into well A.

The configuration can also comprise a combination of the above instructions to allow the injection of fluids having specified properties to begin or end at certain times, or to be performed in a specified order.

A decision on whether to implement a low salinity waterflood is often taken early on in the reservoir planning or development. The indication of the effectiveness of performing the low salinity waterflood that is generated can be used to determine an operating condition such as instructing the installation of desalination equipment, in which case a most basic operating condition is one relating to actual installation. As regards existing and already installed desalination equipment, if the calculated diffusion degrade factor F indicates that a low salinity waterflood would not be sufficiently effective to warrant the operation of desalination equipment, the operating condition can reflect this in the form of an instruction not to operate or employ the existing desalination equipment.

The point at which an installation decision is made varies depending on the type of oilfield site, but, as noted above, embodiments allow this decision to be made as early in the planning process as possible, and avoid wasting time and resources on installing the equipment unnecessarily. For example, for a green field site where low salinity waterflooding is to be implemented in secondary mode, the desalination equipment will be included in the facilities from "day one", that is, a decision to install the desalination equipment is taken when designing an offshore platform and associated equipment. For an offshore brown field site with low salinity waterflooding implemented in tertiary mode, the desalination equipment may be a retrofit to a platform or even located on a separate floating vessel if there are space or weight restrictions on the platform.

Once installed, the operating condition for the desalination equipment can include instructing the desalination equipment to produce a particular quantity of desalinated water or to produce desalinated water having a particular salinity and a particular multivalent cation content.

In instructing the production of a particular quantity of low salinity water, the system can be configured to take into account additional factors such as an available quantity of low salinity water, how much extra low salinity injection fluid is required and the production capacity of the desalination equipment.

Additional injection fluid may be required in order to maintain reservoir pressure; the system can also take this into account when configuring operating conditions for both the injection equipment and the desalination equipment, in order to ensure the efficient treatment and injection of the correct quantity and quality of fluids. For example, the system may configure the desalination equipment to produce enough low salinity water to carry out the waterflood, while the injection equipment may be configured to inject this low salinity water and follow it with a higher salinity fluid such as seawater or produced water in order to suitably maintain the pressure of the reservoir. The system therefore configures and instructs the desalination and injection equipment to balance the different types of fluid being injected at different times and places, in order to optimise the technical resources available.

During initial reservoir appraisal or planning of an oilfield, hypothetical values of the interwell distance L and superficial velocity v of the low salinity water through the relatively permeable layers can be used in configuring the operating conditions of the equipment; the hypothetical interwell distance L is based on potential well locations within the reservoir that are identified during the initial reservoir appraisal and, if required, measurement data from the reservoir. Other parameters such as the diffusion coefficient $D_a$ and the thicknesses $w_n$ of the sandstone layers are obtained and, as explained with reference to Equations 1 to 6 above, the effectiveness of a low salinity waterflood may be determined by calculating the diffusion degrade factor F for the reservoir. Should the generated indication of the effectiveness confirm that a sufficiently effective low salinity waterflood is likely to result, the potential well locations can be confirmed by the system as being acceptable. The system can then use this data to repeat the process for different positions in order to determine other suitable, or even optimal, injection and production well locations, for example by reducing the hypothetical interwell distance L or by moving the potential well positions to a different region of the reservoir having fewer or thinner relatively impermeable layers, to obtain a new indication of the effectiveness of performing a low salinity waterflood; the new indication can then be used by the system to configure alternative, improved or optimised operating conditions. Similarly, the position of an infill well in an existing oilfield, both in terms of its location in the reservoir and its position in relation to existing wells, can be determined and optimised by the system, for example after commencement of the low salinity waterflood. In an offshore environment, there may be relatively few injection wells and production wells, so placement of these wells is critical. A produced water disposal well is likely to be located in a region of the reservoir where modelling shows the lowest effectiveness of performing a low salinity waterflood.

In the foregoing embodiments of the invention, the calculations are described as being performed in the processing unit 202, however this is not a requirement. Equally, while the processing unit has been described as a single, stand-alone, unit, this may not be the case, and for example the functionality of the processing unit may be incorporated into any other entity, or be distributed across a number of entities. The LSW software components are described as being stored in the memory 208, however the LSW software components may alternatively be received via the network interface 212 (from e.g. a remote database). The outputs may be provided to various other entities, such as the well control apparatus. The mechanisms by which this may be done will be well known to the skilled person.

While the above embodiments have been described in relation to the diffusion degrade factor F, which defines the ratio of oil recovery with and without diffusion, it will be apparent that an alternative "diffusion loss factor" (G) may be used which defines the ratio of 'lost' oil to the total oil recovery. Consequently, G may be defined as G=1−F=2x/H. It will be apparent that G and F have a very simple relationship; therefore, the skilled person would have no difficulty in using either in embodiments of the invention.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims. The features of the claims may be combined in combinations other than those specified in the claims.

Additional Applications of Equations

Further applications of Equations 1 to 6 will now be described.

In addition to determining the diffusion degrade factor F, the boundary layer thickness x can be used to calculate a target or threshold superficial velocity for the low salinity waterflood. This may be of use since, as mentioned above, the superficial velocity of the waterflood may be varied by changing e.g. the injection pressure; therefore by providing a target, or a minimum velocity threshold, the effectiveness of the low salinity waterflood can be assured.

Firstly, by combining Equations 3 and 5, reproduced here:

$$x = 2A\sqrt{\frac{D_a L}{v}} \quad \text{(Equation 3)}$$

$$F = 1 - \frac{2x}{H} \quad \text{(Equation 5)}$$

A relationship between the superficial velocity v and the degrade factor F can be established, specifically:

$$H(1-F) = 2x = 4A\sqrt{\frac{D_a L}{v}} \quad \text{(Equation 7)}$$

Equation 7 can be rearranged to produce Equation 8:

$$v = 16\frac{D_a L A^2}{H^2(1-F)^2} \quad \text{(Equation 8)}$$

It is desirable to ensure that the velocity is sufficiently high to maintain the diffusion degrade factor F at, around, or above a desired target or limit. Therefore, taking $F_{target}$ as the target value for the diffusion degrade factor F the target velocity $v_{target}$ can be derived as:

$$v_{target} = 16\frac{D_a L A^2}{H^2(1-F_{target})^2} \quad \text{(Equation 8a)}$$

The target velocity $v_{target}$ may then be used in the control of the injection well to ensure that the superficial velocity of the waterflood is kept at, around, or above the target. Various method of doing this will be apparent to the skilled person, for example, the superficial velocity may be kept within a predetermined range around or above the target velocity $v_{target}$, alternatively the superficial velocity may be controlled to always be above the target velocity $v_{target}$ with other factors (if required) determining a maximum velocity.

As mentioned above, the diffusion degrade factor F represents the proportion of additional oil recovered by the low salinity waterflooding with diffusion taken into account against the case where diffusion of ions is ignored. As such, it represents a measure of the potential success of the waterflooding. Consequently, the target value for the diffusion degrade factor $F_{target}$ may be used to represent a minimum acceptable or ideal value which should be achieved for the waterflooding to be successful (whether practically, in terms of e.g. the amount of low salinity water available, or economically). As a consequence, maintaining the velocity of the waterflood to be above or at the target velocity will ensure that the effectiveness of the waterflood is equally above or at the target.

Figure 5:
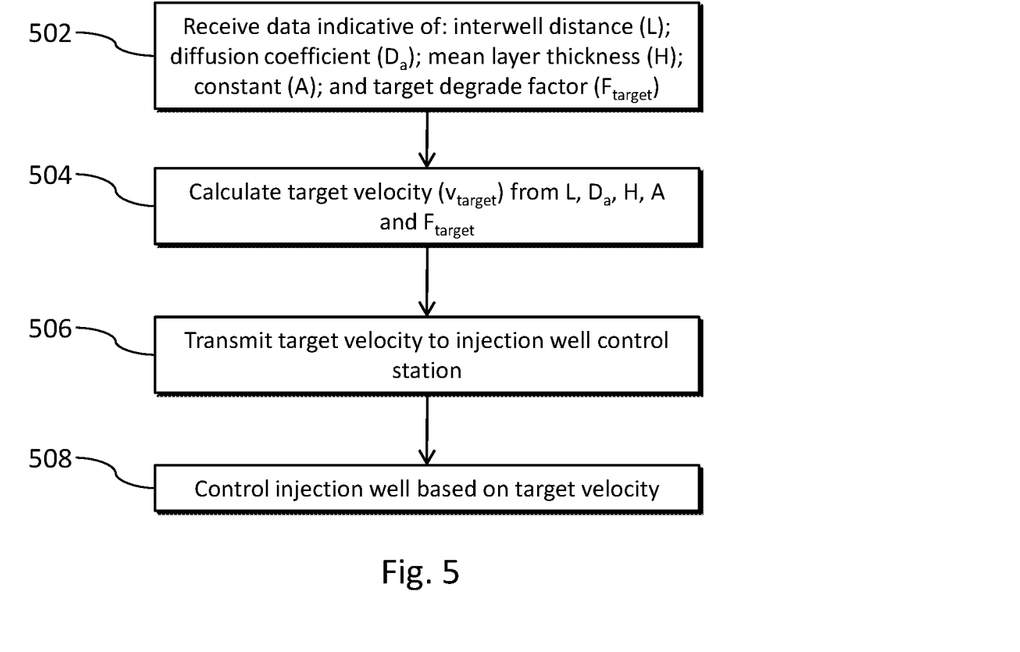
FIG. 5 shows an example of computer implemented method of controlling a low salinity waterflood.

A computer implemented method of controlling a low salinity waterflood will now be described with reference to FIG. 5. As described above with reference to FIG. 4, the steps below may be performed by processor 204 while executing the LSW software components 209.

In step 502 the processor receives data indicative of the interwell distance (L), diffusion coefficient ($D_a$), the mean layer thickness (H), the constant (A), and the target diffusion degrade factor ($F_{target}$). As described above, the mean layer thickness (H) may be received directly, or calculated from the individual layer thicknesses ($w_n$).

In step 504 the processor 204 calculates a target superficial velocity ($v_{target}$) from $D_a$, L, H and $F_{target}$. This may be done using equation 8.

The target superficial velocity may then be used to control the injection pressure in the injection well to thereby control the superficial velocity of the waterflood within the reservoir. Consequently, in step 506, the processor 204 may transmit an indication of the target superficial velocity to the injection well using interface 212.

Subsequently in step 508, the control systems in the injection well control the injection well to maintain the superficial velocity of the flood at an appropriate speed in view of the target superficial velocity. This may be done in any number of ways, which will be obvious to the skilled person, and may be done by maintaining the average superficial velocity of the injection fluid at the target superficial velocity, or by ensuring that the superficial velocity of the flood is kept above the target superficial velocity.

Finally, a computer implemented method of determining the locations of the production injection wells will be described with reference to FIG. 6.

As described above with reference to Equations 8 and 8a, a target superficial velocity may be derived. Equation 8 may be rearranged so that a target interwell length can be derived. Specifically equation 8 can be rearranged as:

$$L = \frac{H^2(1-F)^2 v}{16 D_a A^2} \quad \text{(Equation 9)}$$

which provides the target length as:

$$L_{target} = \frac{H^2(1-F_{target})^2 v}{16 D_a A^2} \quad \text{(Equation 9a)}$$

This target length $L_{target}$ may be calculated from an average value for the superficial velocity (v) as discussed above.

Figure 6:
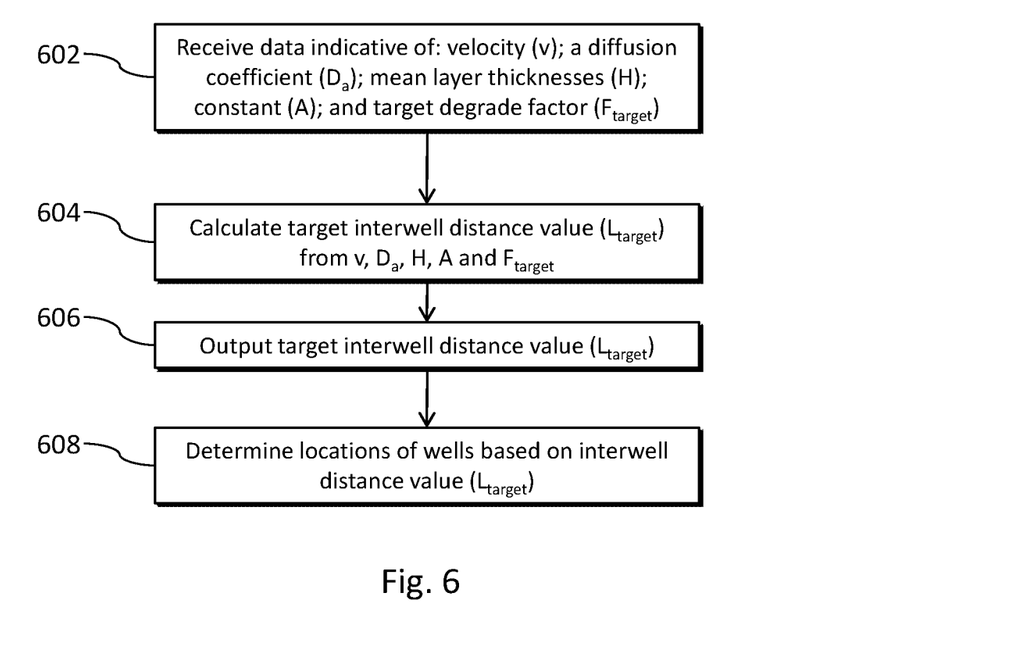
FIG. 6 shows an example of a computer implemented method of determining locations of the production and injection wells.

Therefore, with reference to FIG. 6, in step 602 the processor 204 receives data indicative of the diffusion coefficient ($D_a$), the superficial velocity (v), the mean layer thickness (H), the constant (A), and the target diffusion degrade factor ($F_{target}$). The mean layer thickness (H) may be received directly, or calculated from the individual layer thicknesses ($w_n$).

From these values, using Equation 9, the processor 204 derives a target interwell length ($L_{target}$). This length, being a target, may represent a maximum value for the interwell length, or may represent the centre point for a desired range of interwell lengths (for example, $L_{target}\pm 10\%$).

In step 706 the processor 204 may output the target interwell length ($L_{target}$). In a similar manner to that described above, the value $L_{target}$ may be output using the interfaces 210 and 212. Alternatively the value L may be used directly by the processor 204.

Finally, in step 706, the target interwell length ($L_{target}$) is used in locating the wells penetrating the reservoir. The wells may be located such that the interwell length is less than the target length, or is within a predetermined factor of the length. The exact mechanism to locate the wells which is to be used will depend on a number of other factors, however the target interwell length can be considered as a guide to ensure that low salinity waterflooding will be a possibility when the wells are in production (for the reasons stated above). This step may be performed by processor 204; however it equally may be performed by a separate processing system which is tasked with determining well locations.

What is claimed is:

1. A computer-implemented method for configuring operating conditions for at least one of desalination equipment or fluid injection equipment to be used in a low salinity waterflood on a hydrocarbon-bearing reservoir, wherein the reservoir comprises relatively permeable layers interbedded with relatively impermeable layers and is penetrable by an injection well and a production well, the low salinity waterflood comprising injecting low salinity water into the hydrocarbon-bearing reservoir from the injection well whereby to pass through the relatively permeable layers of the reservoir from the injection well to the production well, and wherein the relatively impermeable layers have a relatively high concentration of ions compared to that of the relatively permeable layers when the low salinity water is present therein, the method comprising configuring at least one processor and at least one memory including computer program code to cause the at least one processor to:

derive an ion diffusion distance value from: a diffusion coefficient indicative of a rate of diffusion of ions through the relatively permeable layers when the low salinity water is present therein; and a residence time value indicative of the time required for the low salinity water to pass from the injection well to the production well through the reservoir;

compare the thickness of the relatively permeable layers to the derived ion diffusion distance value;

generate, based on a result of the comparison, an indication of the effectiveness of performing a low salinity waterflood;

configure, based on the indication of the effectiveness, operating conditions for at least one of desalination equipment or fluid injection equipment to be used in said low salinity waterflood; and instruct the at least one of the desalination equipment or the fluid injection equipment to inject one or more fluids into the injection well, wherein the fluid is injected into the injection well.

2. The method of claim 1, comprising:

determining an average thickness of the relatively permeable layers; and calculating a ratio of the ion diffusion distance value to the average thickness, whereby to compare the thickness of the relatively permeable layers to the derived ion diffusion distance value.

3. The method of claim 2, wherein an output value based on the calculated ratio is output whereby to generate the indication of the effectiveness of performing a low salinity waterflood.

4. The method of claim 3, wherein the output value is calculated from $$1 - \frac{x}{H}$$

where x is the ion diffusion distance value and H is said average thickness.

5. The method of claim 1, wherein the residence time value is calculated from an interwell distance between an injection well location and a production well location, and a velocity at which the low salinity water passes through the reservoir.

6. The method of claim 5, wherein the ion diffusion distance value is determined from $2A\sqrt{(D_a L v^{-1})}$ wherein $D_a$ is the apparent diffusion coefficient for ions in the relatively permeable layers, L is the interwell distance, v is the velocity of the low salinity water through the reservoir, and A is a constant.

7. The method of claim 6, wherein the predetermined constant A has a value in the range of 0.125 to 2.

8. The method of claim 6, wherein the predetermined constant A has a value of 0.5.

9. The method of claim 5, wherein:

at least one of the injection well location or the production well location are potential well locations and the interwell distance is a hypothetical interwell distance; and the velocity of the low salinity water through the reservoir is a hypothetical velocity indicative of a superficial velocity of the low salinity water through the relatively permeable layers.

10. The method of claim 9, wherein the method comprises confirming, based on the generated indication of the effectiveness, that the potential well locations are expected to give rise to an effective low salinity waterflood.

11. The method of claim 1, wherein configuring operating conditions for the fluid injection equipment comprises at least one of:

instructing the fluid injection equipment to inject one or more particular fluids into one or more particular injection wells;

instructing the fluid injection equipment to start or stop injection of fluid into one or more injection wells;

instructing the fluid injection equipment to inject a particular quantity of fluid into one or more injection wells; or instructing the fluid injection equipment to inject one or more particular fluids into one or more injection wells in a specified order.

12. The method of claim 10, wherein said one or more particular fluids comprise one or more of: desalinated water having a particular salinity and a particular multivalent cation content; water produced from the reservoir; and seawater.

13. The method of claim 1, wherein configuring operating conditions for the desalination equipment comprises instructing installation of the desalination equipment at the hydrocarbon-bearing reservoir.

14. The method of claim 1, wherein configuring operating conditions for the desalination equipment comprises instructing the desalination equipment to produce a particular quantity of desalinated water.

15. The method of claim 1, wherein configuring operating conditions for the desalination equipment comprises instructing the desalination equipment to produce desalinated water having a particular salinity and a particular multivalent cation content.

16. The method of claim 1, comprising using the indication of the effectiveness of performing a low salinity waterflood to calculate an estimate for the recovery of hydrocarbons from the reservoir.

17. The method of claim 1, wherein the relatively permeable layers comprise sandstone layers, and the relatively impermeable layers comprise shale layers.

18. A computer readable storage medium storing computer readable instructions thereon for execution on a computing system to implement a method for configuring operating conditions for at least one of desalination equipment or fluid injection equipment to be used in a low salinity waterflood on a hydrocarbon-bearing reservoir, wherein the reservoir comprises relatively permeable layers interbedded with relatively impermeable layers and is penetrable by an injection well and a production well, the low salinity waterflood comprising injecting low salinity water into the hydrocarbon-bearing reservoir from the injection well whereby to pass through the relatively permeable layers of the reservoir from the injection well to the production well, and wherein the relatively impermeable layers have a relatively high concentration of ions compared to that of the relatively permeable layers when the low salinity water is present therein, the method comprising configuring at least one processor and at least one memory including computer program code to cause the at least one processor to:

derive an ion diffusion distance value from: a diffusion coefficient indicative of a rate of diffusion of ions through the relatively permeable layers when the low salinity water is present therein; and a residence time value indicative of the time required for the low salinity water to pass from the injection well to the production well through the reservoir;

compare the thickness of the relatively permeable layers to the derived ion diffusion distance value;

generate, based on a result of the comparison, an indication of the effectiveness of performing a low salinity waterflood;

configure, based on the indication of the effectiveness, operating conditions for at least one of desalination equipment or fluid injection equipment to be used in said low salinity waterflood; and instruct the at least one of the desalination equipment or the fluid injection equipment to inject one or more fluids into the injection well, wherein the fluid is injected into the injection well.

* * * * *